US009946893B2

(12) United States Patent
Nolan et al.

(10) Patent No.: US 9,946,893 B2
(45) Date of Patent: Apr. 17, 2018

(54) METHOD AND APPARATUS FOR PROVIDING PRIVACY PROFILE ADAPTATION BASED ON PHYSIOLOGICAL STATE CHANGE

(71) Applicant: Nokia Corporation, Espoo (FI)

(72) Inventors: Julian Nolan, Pully (CH); Matthew John Lawrenson, Espoo (FI); Debmalya Biswas, Lausanne (CH)

(73) Assignee: Nokia Technologies Oy, Espoo (FI)

( * ) Notice: Subject to any disclaimer, the term of this patent is extended or adjusted under 35 U.S.C. 154(b) by 57 days.

(21) Appl. No.: 14/090,674

(22) Filed: Nov. 26, 2013

(65) Prior Publication Data
US 2015/0150074 A1 May 28, 2015

(51) Int. Cl.
*G06F 21/00* (2013.01)
*G06F 21/62* (2013.01)
(Continued)

(52) U.S. Cl.
CPC ...... *G06F 21/6245* (2013.01); *G06F 19/3418* (2013.01); *G06Q 50/00* (2013.01);
(Continued)

(58) Field of Classification Search
CPC ..... A61B 5/1118; A61B 5/0022; G06F 17/00; G06F 1/163; G06F 17/30528; G06F 2203/011; G06F 11/3438; H04L 63/10
See application file for complete search history.

(56) References Cited

U.S. PATENT DOCUMENTS 5,564,429 A * 10/1996 Bornn ............... A61B 5/0006
379/38
6,611,206 B2  8/2003 Eshelman et al.
(Continued)

FOREIGN PATENT DOCUMENTS

WO  2006043925 A1  4/2006
WO  2013097367 A1  7/2013

OTHER PUBLICATIONS

Samuel A. et al. "Context-Aware Adaptation of Access-Control Policies" IEEE Computer Society, Jan./Feb. 2008, pp. 51-54.
(Continued)

*Primary Examiner* — Lisa Lewis
*Assistant Examiner* — Christopher C Harris
(74) *Attorney, Agent, or Firm* — Ditthavong & Steiner, P.C.

(57) ABSTRACT

An approach is provided for adapting privacy profiles to respond to changes in physiological state. The policy platform may process and/or facilitate a processing of sensor information to determine at least one change in one or more physiological states of at least one user, wherein the at least one user is associated with at least one context, at least one activity, or a combination thereof. Then, the policy platform may cause, at least in part, a modification of at least one privacy profile for at least one device associated with the at least one user based, at least in part, on the at least one change in the one or more physiological states, the at least one context, the at least one activity, or a combination thereof, wherein the modification of the at least one privacy profile includes, at least in part, an enabling or a disabling of one or more privacy services operating at least at least one device.

14 Claims, 13 Drawing Sheets

(51) Int. Cl.

| | | |
|---|---|---|
| *H04L 29/06* | (2006.01) | |
| *G06F 19/00* | (2018.01) | |
| *G06Q 50/00* | (2012.01) | |
| *G06F 1/16* | (2006.01) | |
| *G06F 17/30* | (2006.01) | |
| *G06F 11/34* | (2006.01) | |

(52) U.S. Cl.
CPC .............. *H04L 63/10* (2013.01); *G06F 1/163* (2013.01); *G06F 11/3438* (2013.01); *G06F 17/30528* (2013.01); *G06F 2203/011* (2013.01)

(56) References Cited

U.S. PATENT DOCUMENTS

| | | | |
|---|---|---|---|
| 8,655,307 B1* | 2/2014 | Walker et al. ................ 455/405 | |
| 2004/0147814 A1* | 7/2004 | Zancho ................ H04M 19/04 | 600/300 |
| 2005/0138420 A1* | 6/2005 | Sampathkumar ...... G06Q 10/10 | 726/4 |
| 2006/0053377 A1 | 3/2006 | Newell et al. | |
| 2008/0294016 A1* | 11/2008 | Gobeyn ................ A61B 5/103 | 600/301 |
| 2008/0294018 A1 | 11/2008 | Kurtz et al. | |
| 2009/0076341 A1* | 3/2009 | James ................ A61B 5/0002 | 600/301 |
| 2009/0271383 A1 | 10/2009 | Bhamidipaty et al. | |
| 2010/0076777 A1 | 3/2010 | Paretti et al. | |
| 2011/0156875 A1* | 6/2011 | Sugimura .................... 340/10.1 | |
| 2011/0201960 A1 | 8/2011 | Price et al. | |
| 2012/0110680 A1* | 5/2012 | Oliver ................ G06F 21/6245 | 726/30 |
| 2012/0131155 A1* | 5/2012 | Madey et al. ................ 709/220 | |
| 2012/0185419 A1* | 7/2012 | Kuhn et al. ..................... 706/12 | |
| 2012/0222083 A1* | 8/2012 | Vaha-Sipila et al. ............. 726/1 | |
| 2012/0271913 A1* | 10/2012 | Tallgren et al. .............. 709/217 | |
| 2014/0059695 A1* | 2/2014 | Parecki ................... G06F 21/60 | 726/26 |
| 2014/0085101 A1* | 3/2014 | Rahman ............... A61B 5/0022 | 340/870.01 |
| 2014/0361905 A1* | 12/2014 | Sadasivam ............. G08C 17/02 | 340/870.01 |
| 2015/0081695 A1* | 3/2015 | Schillings et al. ............ 707/736 | |
| 2016/0188902 A1* | 6/2016 | Jin ...................... G06F 21/6245 | 726/28 |

OTHER PUBLICATIONS

Schaub F. et al. "Privacy Context Model for Dynamic Privacy Adaptation in Ubiquitous Computing" 6th International Workshop on Context-Awareness for Self-Managing Systems, Sep. 5-8, 2012, pp. 1-6.

* cited by examiner

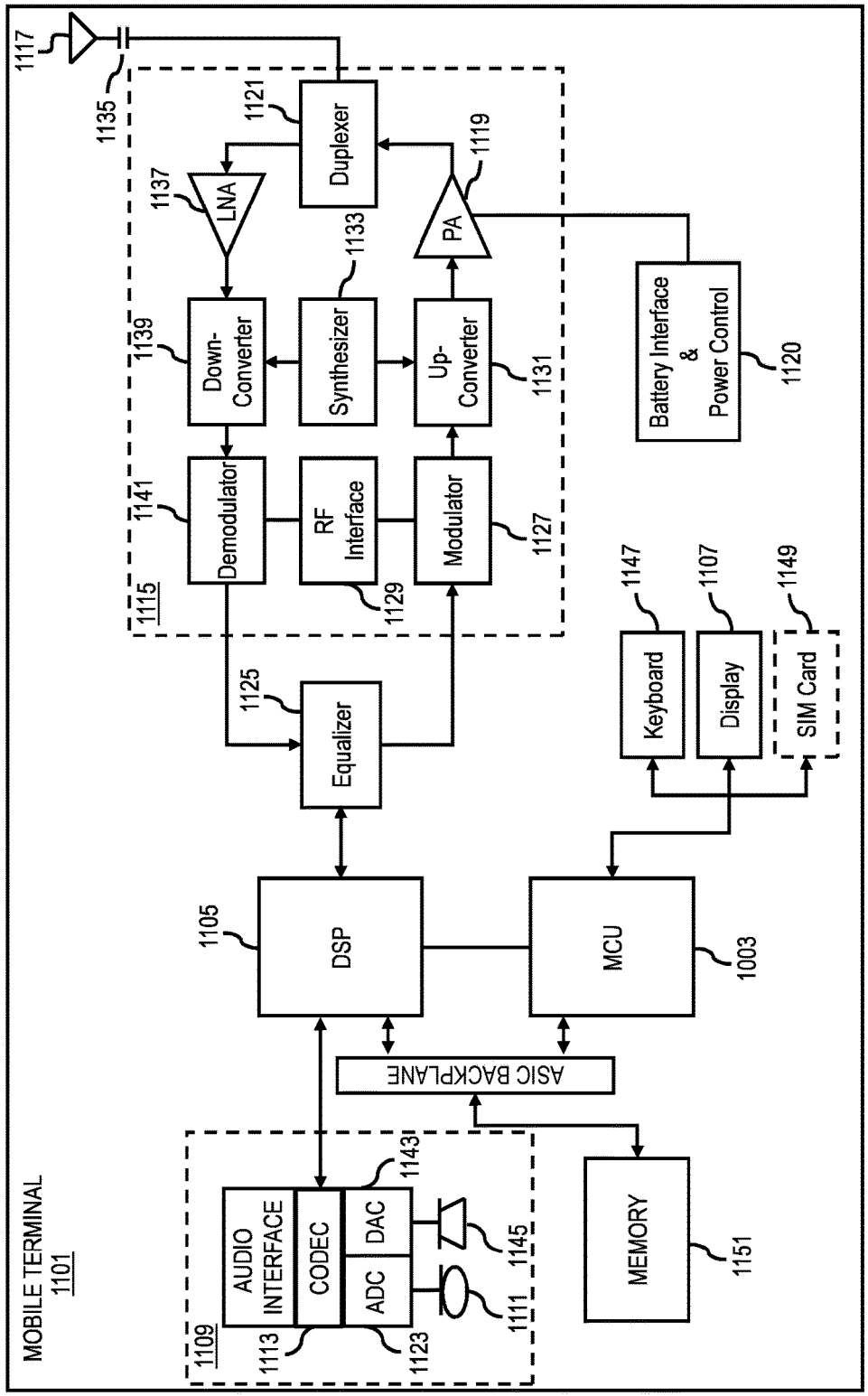

METHOD AND APPARATUS FOR PROVIDING PRIVACY PROFILE ADAPTATION BASED ON PHYSIOLOGICAL STATE CHANGE

BACKGROUND

Service providers and device manufacturers (e.g., wireless, cellular, etc.) are continually challenged to deliver value and convenience to consumers by, for example, providing compelling network services. One area of interest has been the development of connecting devices to respond to physiological states. For example, users often interact with a host of devices and systems such that data intensive services are increasingly ubiquitous. As data intensive services become more popular, users are increasingly reliant on network and data accessibility or sharing. However, privacy concerns often restrict a user's willingness to share data. Due to privacy concerns, users often set privacy policies to restrict data sharing. However, as a user's context or situation changes, changes to the sharing restrictions may better serve a user's service requirements. For instance, stressors put on a user may be alleviated by adapting a data sharing plan that could help offset the stressors. Currently, the user may manually elect to change service requirements. However, users engaged in activities may not pause for manual selection, even when the selection may benefit a situation. Therefore, content providers face challenges in adjusting data sharing to offset stressors applied to a user.

Some Example Embodiments

Therefore, there is a need for an approach for adapting privacy profiles to respond to changes in physiological states.

According to one embodiment, a method comprises processing and/or facilitating a processing of sensor information to determine at least one change in one or more physiological states of at least one user, wherein the at least one user is associated with at least one context, at least one activity, or a combination thereof. The method also comprises causing, at least in part, a modification of at least one privacy profile for at least one device associated with the at least one user based, at least in part, on the at least one change in the one or more physiological states, the at least one context, the at least one activity, or a combination thereof, wherein the modification of the at least one privacy profile includes, at least in part, an enabling or a disabling of one or more privacy services operating at the at least one device.

According to another embodiment, an apparatus comprises at least one processor, and at least one memory including computer program code for one or more computer programs, the at least one memory and the computer program code configured to, with the at least one processor, cause, at least in part, the apparatus to process and/or facilitate a processing of sensor information to determine at least one change in one or more physiological states of at least one user, wherein the at least one user is associated with at least one context, at least one activity, or a combination thereof. The apparatus is also caused to cause, at least in part, a modification of at least one privacy profile for at least one device associated with the at least one user based, at least in part, on the at least one change in the one or more physiological states, the at least one context, the at least one activity, or a combination thereof, wherein the modification of the at least one privacy profile includes, at least in part, an enabling or a disabling of one or more privacy services operating at the at least one device.

According to another embodiment, a computer-readable storage medium carries one or more sequences of one or more instructions which, when executed by one or more processors, cause, at least in part, an apparatus to process and/or facilitate a processing of sensor information to determine at least one change in one or more physiological states of at least one user, wherein the at least one user is associated with at least one context, at least one activity, or a combination thereof. The apparatus is also caused to cause, at least in part, a modification of at least one privacy profile for at least one device associated with the at least one user based, at least in part, on the at least one change in the one or more physiological states, the at least one context, the at least one activity, or a combination thereof, wherein the modification of the at least one privacy profile includes, at least in part, an enabling or a disabling of one or more privacy services operating at the at least one device.

According to another embodiment, an apparatus comprises means for processing and/or facilitating a processing of sensor information to determine at least one change in one or more physiological states of at least one user, wherein the at least one user is associated with at least one context, at least one activity, or a combination thereof. The apparatus also comprises means for causing, at least in part, a modification of at least one privacy profile for at least one device associated with the at least one user based, at least in part, on the at least one change in the one or more physiological states, the at least one context, the at least one activity, or a combination thereof, wherein the modification of the at least one privacy profile includes, at least in part, an enabling or a disabling of one or more privacy services operating at the at least one device.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of any of originally filed claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIG. 11 is a diagram of a mobile terminal (e.g., handset) that can be used to implement an embodiment of the invention.

DESCRIPTION OF SOME EMBODIMENTS

Examples of a method, apparatus, and computer program for adapting privacy profiles to respond to changes in physiological states are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Figure 1:
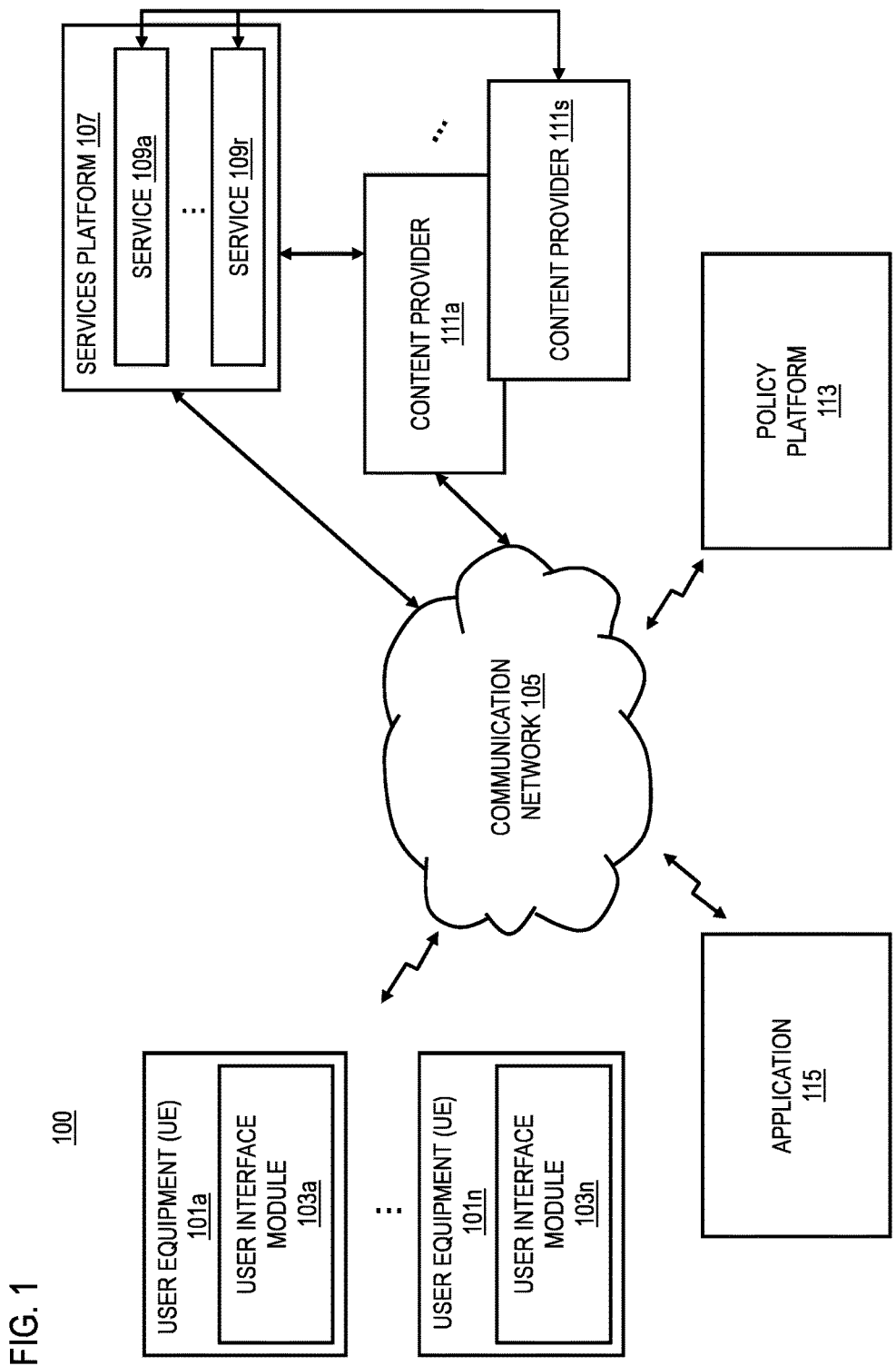
FIG. 1 is a diagram of a system capable of adapting privacy profiles to respond to changes in physiological states, according to one embodiment.

FIG. 1 is a diagram of a system capable of adapting privacy profiles to respond to changes in physiological state, according to one embodiment. Service providers and device manufacturers (e.g., wireless, cellular, etc.) are continually challenged to deliver value and convenience to consumers by, for example, providing compelling network services. One area of interest has been the development of connecting devices to respond to physiological states. For example, as data intensive services become more prevalent, users are increasingly reliant on network and data accessibility or sharing. However, users often limit data sharing due to privacy concerns. The concerns are often balanced with a user's need to access an associated service or benefits derived from the service. For example, a user may weigh the benefits versus the privacy concerns regarding user data shared with an autonomous car. In another instance, a lost child may have to decide whether to reveal location information to activate a help beacon, thus possibly disclosing information regarding his age, characteristics, and location. Even on a more simple level, users may determine whether caller identification should be disclosed to a recipient of a telephone call. All are instances where users choose data or information to share based on their privacy concerns.

With the multitude and complexity of data services, users are often uncertain as to the optimal amount of personal data to share with service providers. Currently, data shared as part of privacy policies may be static or unchanging with respect to a user's context or situation. However, in some situation, a relaxing of a privacy policy or increasing sharing or information may better serve a user's service requirements. The current option is for a user to manually adjust privacy settings with respect to his context or activities. Such adjustment may be unrealistic while a user is occupied with activities, even if the change may benefit the user's situation.

Simultaneously, technology is available to detect users' physiological changes or moods. For example, devices with sensors to provide insight on sleep habits, exercise habits, dietary consumption, etc. are increasingly available. However, content providers face challenges in adjusting data sharing to respond to changes in a user's situation, for instance, with respect to changes in a user's physiological state.

To address this problem, a system 100 of FIG. 1 introduces the capability to adapt privacy profiles to respond to changes in physiological state, according to one embodiment. System 100 may sense a user's current context and identify privacy policies that may be adapted to assist a user's situation. In one embodiment, system 100 may assist a user's situation in terms of a user's physiological state. For example, system 100 may adapt privacy policies with respect to measured anticipated benefits to a user's physiological state.

In one embodiment, system 100 may create a relationship between physiological states, user contexts and activities, and privacy profiles. In one embodiment, the system 100 may automatically prompt information sharing based on a user's physiological state (or change in physiological state).

For instance, system 100 may detect that a user is stressed. In response, the system 100 may share a category of information that could alleviate the stress. For example, the physiological state of stress may be associated with some user activity. For instance, the system 100 may include various sensors to detect physiological states. Such sensors may include biological sensors, including sensors detecting heart rate or motion or perspiration. In a further example, system 100 may define various activities that users may take or contexts where a user may be situated. The system 100 may create associations between the activities, contexts, and physiological states. For example, the system 100 may associate the activity "driving" with a "relaxed" physiological state. In a further example, "driving" may be associated with a physiological state of "relaxed" in a context denoting a weekend. However, driving in the context of rush hour may be associated with a physiological state, "stress."

Based on associations between physiological states, contexts, and user activities, the system 100 may modify privacy profiles in response to changes in physiological states. For example, the system 100 may evaluate physiological benefits that may be derived from enabling or disabling parts of privacy profiles, then enact these modifications to improve the physiological state of a user. For instance, the system 100 may first determine privacy policies. In one case, privacy policies may include the criteria and available settings for various types of data. Privacy policies may include various sets of data sharing capabilities available from service providers. Policy profiles may denote privacy settings with respect to specific users. For example, policy profiles may include data sharing requirements set by users, for various services. For instance, a policy profile of a user may denote data from various services that may be shared or that cannot be shared.

In implementation, the system 100 may first monitor a user's context, including the user's physiological state. For instance, the system 100 may use sensors that are part of a mobile user device. For instance, various phone applications have capabilities to monitor biological sensors including heart rate, motion, perspiration, etc. In some scenarios, a user's physiological state may comprise a user's context. In other scenarios, user's context may further include factors including time of day, location, recent physical activity or recent interaction with a user device, etc. Context information may include any information regarding a user's environment or surroundings. Then, the system 100 may correlate physiological states to user activities and/or context. For example, system 100 may determine various groupings of activities. For example, "exercise," "eating," "driving," or "travel." Similarly, system 100 may identify various contexts including, "work," "home," "night," "day," etc. In one embodiment, system 100 may determine physiological states associated with these activities and/or contexts, and further determine changes in physiological states. For example, for a particular user, system 100 may generally associate "exercise" with a physiological state, "happy." However, if physiological state sensors indicate a change from "happy" to a negative physiological state, system 100 may note the change.

In one embodiment, system 100 may note the change and respond with a modification to a policy profile. To know what modification to make, system 100 may first determine candidate user actions that can be performed to offset negative physiological state changes. For instance, system 100 may engage generic behavioral models, in addition to records of historical user actions, to determine candidate user actions. Candidate user actions may include actions that a user may take following a negative physiological state change, to improve the physiological state change. For example, user A may be engaging in the activity of driving to the airport. User A may be running late and caught in traffic in a non-priority late. System 100 may determine that user A's physiological state changed to being negative as the car slows down and user A is increasingly stressed. Then, system 100 may determine that one candidate user action is for a user to use a priority lane to speed his travel. System 100 may further determine context information where the highway traveled by user A is part of a local highway authority scheme where road users that share their geo-routines may user a priority lane. Then, system 100 may prompt a modification in user A's privacy profile to allow location sharing, such that user A may then user the priority lane in accordance to the highway scheme. In doing so, system 100 makes the privacy profile modification that permits user A to take a candidate action that may offset his negative change in physiological state.

In other words, system 100 may determine negative and positive changes to physiological states. Then, system 100 may also identify candidate actions that a user may take to counteract the changes. In particular, the system 100 may determine actions to offset negative changes in physiological state. For instance, if a user changes from a "calm" physiological state to a "stressed" physiological state, system 100 tries to respond in order to restore the "calm" physiological state. To respond, system 100 may determine adjustments to users' privacy profiles in order to share information that may facilitate or bring about a user action that may alleviate the stress. System 100 may identify sets of such response actions, given physiological states, user activities, and contexts. For example, the system 100 may map physiological state changes to particular user activities or environments. The mapping may be based on clustering or mining techniques, for instance. Based on the particular physiological state changes and respective user activities and/or user context, the system 100 may identify candidate user action that a user may take subsequent to the physiological state change. Such candidate user actions are actions that can restore the user's physiological state to a state prior to the change.

In one embodiment, system 100 may structure the mapping as a matrix based on user context and/or activity associated to user physiological state. Candidate user actions may be a further component of the matrix. Yet another aspect includes determining what functions or portions of privacy profiles to enable or disable in connection with the candidate user actions.

One use case may include a hiker who is lost. The hiker may have a map installed on her mobile phone, but her privacy profile may be set such that the map does not indicate her present location information. System 100 may determine that the hiker's context is an unusual trajectory for hiking in the area and that intersections (in paths) are associated with negative changes in her physiological state. Here, the physiological state change may include negative physiological reactions where the hiker must decide what path to choose, user activity may include "hiking" or "hiking at state park X," and context may include, for instance, "state park X." Based on the knowledge of the physiological state, user activity and context, system 100 may determine that a candidate user action is for the hiker to see her location on a map. Another candidate user action can be for the hiker to poll her friends or social network for suggestions as to landmarks or distances so that she can regain her bearings.

Based on the candidate user actions, system 100 may determine data sharing requirements to bring about or supplement the user actions. For example, to locate herself on a map, the hiker must share her location information with the map application on her mobile phone. To receive help from friends, the hiker should share her location information with her friends. First, system 100 may evaluate whether the user's privacy profile accommodates the data sharing requirements. For example, the hiker may have her privacy profile such that her location information is shared with friends. Then to receive help from friends, no modification to her privacy profile is needed. Alternately, the system 100 may determine that a privacy profile must be modified to satisfy the data sharing requirements. Then, system 100 may cause at least one modification to a privacy profile in order to share the data.

In one embodiment, candidate user actions may be determined based on past user behavior, including actions found from user history. For example, system 100 may note that a user has responded to a particular scenario in the past in a way to change his physiological state. System 100 may then note this response as a candidate user action in the future to determine what data to share or what modification to make to at least one privacy profile.

Another user case includes a user X sharing geo-location information on a social network so that friends can find him. However, system 100 may detect that user X experiences negative physiological changes when friend Y is proximate user X. Then, system 100 may sense that user X should perhaps avoid friend Y as a candidate user action. In terms of privacy profiles, system 100 may prompt user X to stop sharing his geo-location information with friend Y. If user X approves the change in data sharing, system 100 may make the modification to user X's privacy profile to disable the sharing of user X's geo-location information with respect to friend Y. The restriction may be temporary or an updated privacy profile, adapted to include the restriction to friend Y until further notice.

In one embodiment, system 100 may automatically make the modifications to privacy profiles. In another embodiment, system 100 may present users with recommendations, especially with respect to candidate user actions and modifications. For example, system 100 may offer a display that highlights to a user, one or more candidate user actions, the user's current and anticipated physiological state, and data that needs to be shared (along with corresponding privacy profile modification).

In one embodiment, the modification may be temporary or last only as long as the physiological state changes. For example, if a physiological state changes from "calm" to "excited," the modification may last only as long as the user is "excited." In another embodiment, system 100 sets the modification to last for duration of a pre-set time or expiration time. The expiration time may be configured by the user and/or based on generic models on how long users, as a population, usually take to return to a stable physiological state after experiencing the cause of stress.

As shown in FIG. 1, the system 100 comprises a user equipment (UE) 101*a*-101*n* (or UEs 101) having connectivity to user interface modules 103*a*-103*n* (or user interface modules 103), a services platform 107 comprised of services 109*a*-109*r* (or services 109), content providers 111*a*-111*s* (or content providers 111), a policy platform 113, and an application 115 via a communication network 105. By way of example, the communication network 105 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

The UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. It is also contemplated that the UE 101 can support any type of interface to the user (such as "wearable" circuitry, etc.).

In one embodiment, the user interface modules 103 may provide sensor information to the policy platform 113. In one embodiment, the policy platform 113 may automatically receive sensor information from UEs 101, for example via application 115. In another embodiment, user interface modules 103 permit users to dictate or at least alter sensor information that is received by policy platform 113. In yet another embodiment, user interface modules 103 interact with policy platform 113 where user interface modules 103 may present modifications to privacy profiles as recommendations. As an initial step, user interface modules 103 may permit users to create their initial privacy settings for their privacy profiles, especially profiles with respect to specific services 109. Then, policy platform 113 may prompt user interface modules 103 to present one or more recommendations for privacy profile modifications when the policy platform 113 detects a change in physiological state.

In a further embodiment, user interface modules 103 may provide policy platform 113 with user activity and/or context information. For instance, user activity information may include a user's activity on a social network (e.g. posting, commenting, sharing, etc.). Context information may also be derived from user interface modules 103, for instance, where users "check in" to a location or provide a timestamp on some activity. Then, the user interface modules 103 may permit policy platform 113 to construct stronger associations between physiological states, activities, and contexts, as well as more accurate candidate actions and data sharing requirements.

In one embodiment, the services platform 107 may provide services 109 that for various forms of data usage. For example with the use case of a user who is lost and in need of a map, services 109 may be a map application that provides mapping and/or navigation services. In one embodiment, user privacy profiles may be specific to each service 109. For example, for a map application service 109a, a user may have a privacy profile set to share all of his location information whereas that location information may be restricted for another map application service 109b. In another embodiment, services 109 may deduce privacy profile settings based on user settings with similar or analogous services using the same data. For instance, one music-related service 109c may have access to all music downloaded by a user. Then, if the user engages another music-related service 109d, service 109d may default to having the privacy profile for the user where the service 109d may access all music downloaded by the user unless the user changes the settings.

In one embodiment, the content providers 111 may provide the generic behavioral models and/or historic user behavior from which the policy platform 113 formulates parameters for physiological states. For example, the content providers 111 may provide the ranges of physiological markers that generally denote particular physiological states. For example, content providers 111 may provide a range of heart rates that constitute an "elevated" heart rate, thus denoting a "stressed" rather than "calm" physiological state. In other words, content providers 111 may provide policy platform 113 with the information needed to determine, from sensor information, one or more physiological states. In another embodiment, policy platform 113 simply has to detect a change in physiological state. System 100 may modify a policy profile based simply on the change and not require a definition from content providers 111 as to definitions of physiological states. However, the definitions of physiological states may permit the system 100 to better anticipate future responses to the changes in physiological states.

In another or further embodiment, content providers 111 may provide generic behavioral models and/or a user's historic behavior in order for the policy platform 113 to determine candidate user actions. For example, content providers 111 may contain a repository of user responses that may form the basis of expected actions taken that offset physiological changes. In one embodiment, the content providers 111 may further develop the behavioral models with respect to various user identities or characteristics, as well as contexts. For example, the content providers 111 may provide generic behavioral models for specific demographics, age, or gender groups.

In one embodiment, the policy platform 113 may adapt privacy profiles to respond to changes in physiological states. In one embodiment, policy platform 113 may map user context and/or activity associated to at least one physiological state. The policy platform 113 may further determine historical and candidate user actions. Then, the policy platform 113 may determine data sharing requirements in connection with the candidate user actions and cause modifications to privacy profiles based on the data sharing requirements.

In one embodiment, the application 115 may serve as the means by which the UEs 101 and policy platform 113 interacts. For example, the application 115 may activate upon user request or upon prompting from the policy platform 113 that a physiological state change is detected. For example, application 115 may act as the intermediary through which policy platform 113 receives sensor information from UEs 101 and convey privacy profile modifications to UEs 101 back from platform 113.

By way of example, the UE 101, user interface modules 103, services platform 107 with services 109, content providers 111, policy platform 113, and application 115 communicate with each other and other components of the communication network 105 using well known, new or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 2A:
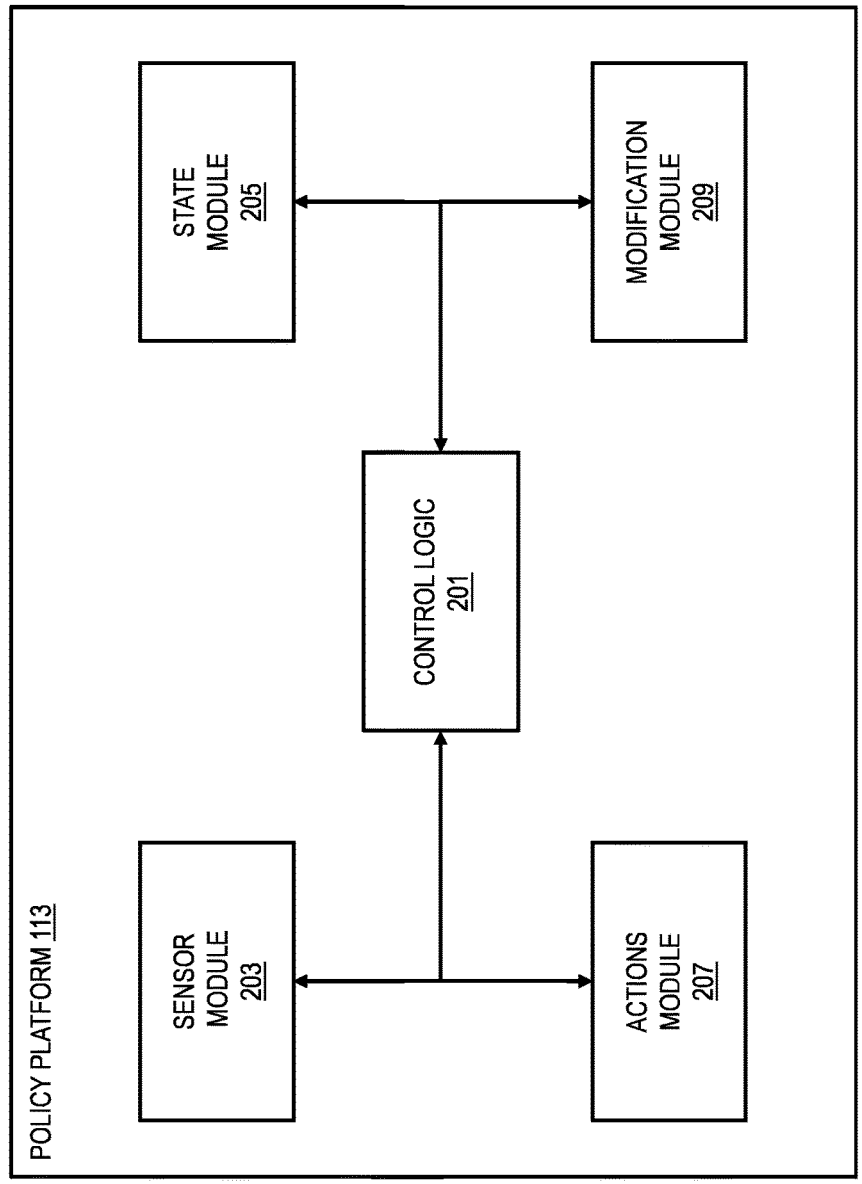
FIG. 2A is a diagram of the components of a policy platform, according to one embodiment.

FIG. 2A is a diagram of the components of the policy platform 113, according to one embodiment. By way of example, the policy platform 113 includes one or more components for adapting privacy profiles to respond to changes in physiological states. It is contemplated that the functions of these components may be combined in one or more components or performed by other components of equivalent functionality. In this embodiment, the policy platform 113 includes a control logic 201, a sensor module 203, a state module 205, an actions module 207, and a modification module 209.

In one embodiment, the control logic 201 and sensor module 203 may determine sensor information available from the UEs 101. For example, various UEs 101 may include biological sensors. Control logic 201 and sensor module 203 may determine sensor information available, as well as groupings of sensor information that may indicate various physiological states. For example, control logic 201 and sensor module 203 may determine that heart rate above a certain threshold may indicate stress or anxiety as physiological states.

In a further embodiment, control logic 201 and sensor module 203 may also detect context and/or activity information. For instance, control logic 201 and sensor module 203 may detect a user's context based on time, location information, temperature information, etc. as provided by UEs 101 associated with a user. In one such case, temperature information may indicate whether the context is night or day and location information may give insight into a user's whereabouts.

In one embodiment, the control logic 201 and state module 205 may determine various physiological states. For example, the control logic 201 and state module 205 may identify physiological states including "stressed," "anxious," "panicked," "calm," relaxed," "happy," etc. In a further example, the control logic 201 and state module 205 may identify sensor information associated with each physiological state. For instance, "stressed" physiological state may include a range of sensor information associated with the state such that the control logic 201 and state module 205 may identify a user with sensor information within that range as being in the "stressed" physiological state. In a further instance, the ranges may also permit control logic 201 and state module 205 to determine changes in physiological state. For example, if a range of sensor information for "stressed" escalates, the change in sensor information may trigger control logic 201 and state module 205 to determine also, a change in physiological state from "stressed" to "panicked."

In one embodiment, the control logic 201 and state module 205 may have physiological states along a spectrum. For instance, the spectrum may span from positive to negative with various states falling in between. For example, the spectrum may list "relaxed," "calm," "anxious," and "panicked" in that order as being most positive to most negative. In one embodiment, control logic 201 may continually modify privacy profiles to move into increasingly positive physiological states. Further, the control logic 201, sensor module 203, and state module 205 may work in conjunction to set sensor information and physiological state determinations particular to specific users. For example, different users may experience emotions and physiological state changes differently. The control logic 201, sensor module 203, and state module 205 may construct ranges of sensor information to correspond to physiological states particular to each user.

In one embodiment, the control logic 201 and actions module 207 may determine first, historical user actions and see how a user generally responds to various physiological states or changes in physiological states. Then, the control logic 201 and actions module 207 may determine candidate user actions. In one embodiment, the control logic 201 and actions module 207 defines actions as actions that can neutralize a negative physiological change.

In one embodiment, the control logic 201 and modification module 209 may determine modifications to privacy profiles to respond to changes in physiological states. For instance, the control logic 201 and modification module 209 may determine the length of time that a modification should last. The control logic 201 and modification module 209 may further determine what data or what types of data to share or not share, as well as what entities and parties may be party to data sharing. Furthermore, the control logic 201 and modification module 209 may track and record modifications approve by users or users' response to modifications. In this way, the control logic 201 and modification module 209 may increasingly anticipate users' preferences with regard to modifications to privacy profiles and/or determine permanent changes to privacy profiles that may benefit a user.

Figure 2B:
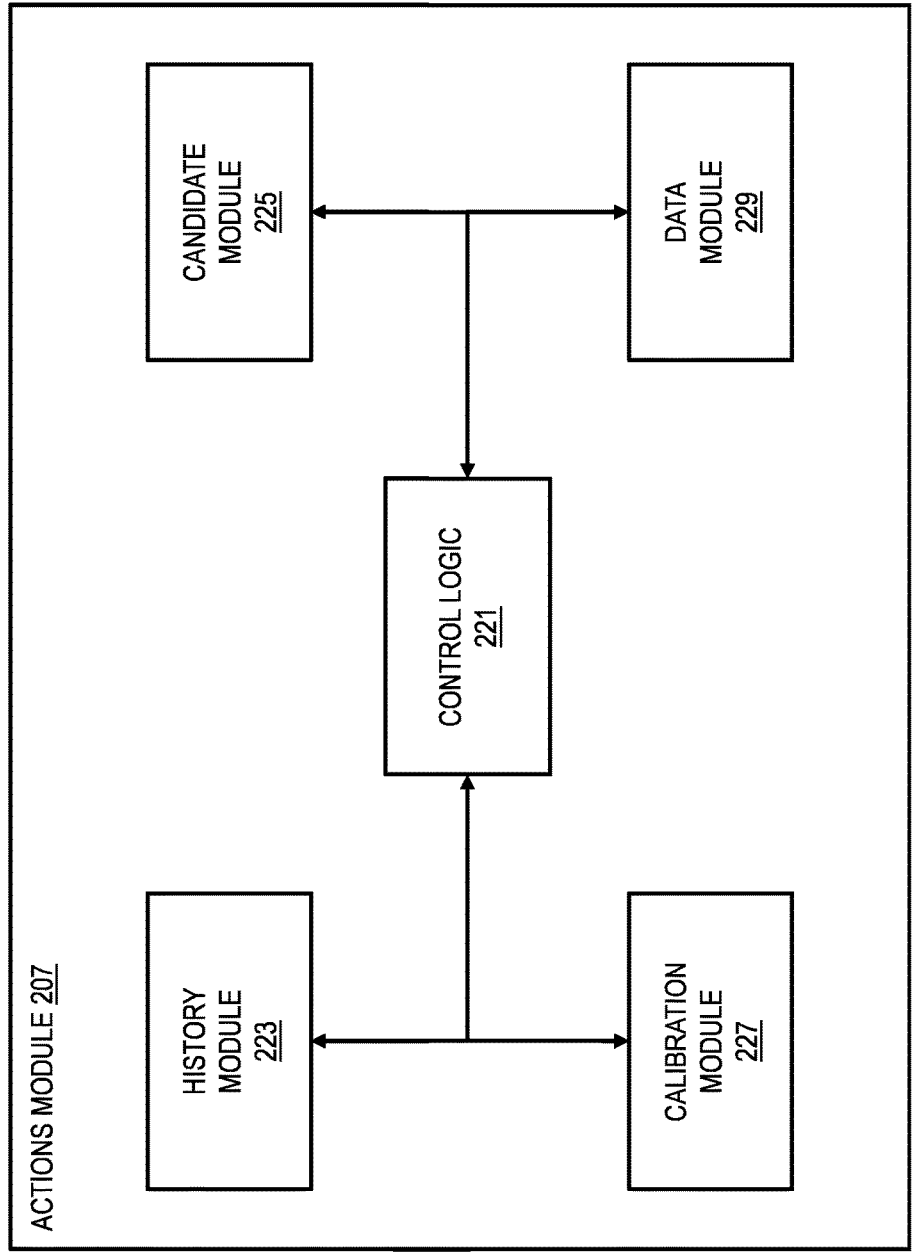
FIG. 2B is a diagram of the components of an actions module, according to one embodiment.

FIG. 2B is a diagram of the components of the actions module 207, according to one embodiment. By way of example, the actions module 207 includes one or more components for determining candidate actions that may offset negative physiological state changes. It is contemplated that the functions of these components may be combined in one or more components or performed by other components of equivalent functionality. In this embodiment, the actions module 207 includes a control logic 221, a history module 223, a candidate module 225, a calibration module 227, and a data module 229.

In one embodiment, the control logic 221 and the history module 223 may determine generic behavioral models as well as historic user actions in relation to physiological states. For example, the control logic 221 and history module 223 may identify various actions that should, based on behavioral models, positively change physiological states. For example, behavioral models may show that hikers that are lost, access maps to find their way. Being lost may cause a change in physiological state from being calm, to being stressed. Then, accessing a map may be an action as identified by the control logic 221 and history module 223 via behavioral models. In one embodiment, historic user actions may offer more fine details as to actions that may be specific to a user. For example, user B may often refer to a specific map service when accessing maps. For instance, the map service may be a map service installed on a mobile device associated with user B. Then, control logic 221 and history module 223 may identify accessing the particular map service on the mobile device as being a historic user action associated with alleviating a "stressed" physiological state.

Furthermore, the control logic 221 and history module 223 may determine deviations from usual user behavior and identify actions that may adjust for the deviations. For example, the control logic 221 and history module 223 may determine that user B is hiking along a route. In one scenario, the control logic 221 and history module 223 may recognize the route since it is hiked by many users and part of a behavioral model or history of many users. In another scenario, the control logic 221 and history module 223 may simply recognize the route from user B's history as a route hiked previously or often by user B. From the expected, known route, the control logic 221 and history module 223 may deduce that where deviations from the route are observed to be connected to sensor information indicating negative physiological changes. The control logic 221 and history module 223 may then determine that part of the action may be to get a user back to the known route.

In one embodiment, the control logic 221 and candidate module 225 may determine actions specific to particular users. In one embodiment, the control logic 221 and history module 223 may give the collection of possible actions to offset physiological state changes. Then, the control logic 221 and candidate module 225 may determine, for a specific user, actions the user may actually take or actions that may apply to the user's particular activity and context. For instance, the control logic 221 and history module 223 may identify "user priority lane on highway" as an action for changing a user's physiological state. However, a user may not be traveling along a highway with a priority lane. Then, control logic 221 and candidate module 225 would identify the action of user a priority lane and not constituting a candidate user action. Alternately, a user may be in a physiological state where some actions that would usually calm the user may only increase his anxiety. For example, a "stressed" user may appreciate sharing some information with a social network for advice whereas a "panicked" user may only get increasingly tense with the same action. Then, control logic 221 and candidate module 225 would not identify asking for recommendations from a social network as being a candidate user interaction in that particular situation. In other words, the control logic 221 and candidate module 225 may determine candidate user actions in relation to user activity, context, and physiological state. Actions that the control logic 221 and candidate module 225 may identify as candidate user actions in one scenario, may not apply in another setting.

In one embodiment, the control logic 221 and calibration module 227 may further ensure that mapping of physiological state change, activities, contexts, and actions are user-specific. For instance, a drastic change in physiological state may be associated with little candidate action for one user, whereas another user may engage in candidate user actions after only minute changes in physiological state. For example, an experienced hiker may feel anxiety from being lost, but see being the anxiety and being lost as part of the adventure of hiking. Then, he may try to find his way on his own and not want intervention by way of location-sharing with map applications, even if he is anxious and lost for an extended period of time. Typical users, however, may have preferred to share location information at a lower threshold of anxiety. The control logic 221 and calibration module 227 may take into account the sensor information particular to each user at which a change in physiological state may warrant system 100 to engage. The control logic 221 and calibration module 227 may then also interact with the history module 223, candidate module 225, and pull in various user-specific information to verify that candidate actions from the candidate module 225 are accurate for a given user.

In one embodiment, the control logic 221 and data module 229 may determine associations between the actions and data that may be shared. For example, with the use case of user B hiking, the action of accessing a map may be associated with location data indicating user B's current location. The action of accessing a map may further include data indicating user B's route or navigation to B's current location. The control logic 221 and data module 229 may even further tie data relating the B's total travel time or when she set out hiking as part of the data associated with the action of accessing the map. In other words, control logic 221 and data module 229 may create the relationship between various actions and data that is shared or not shared based on privacy profiles.

Figure 2C:
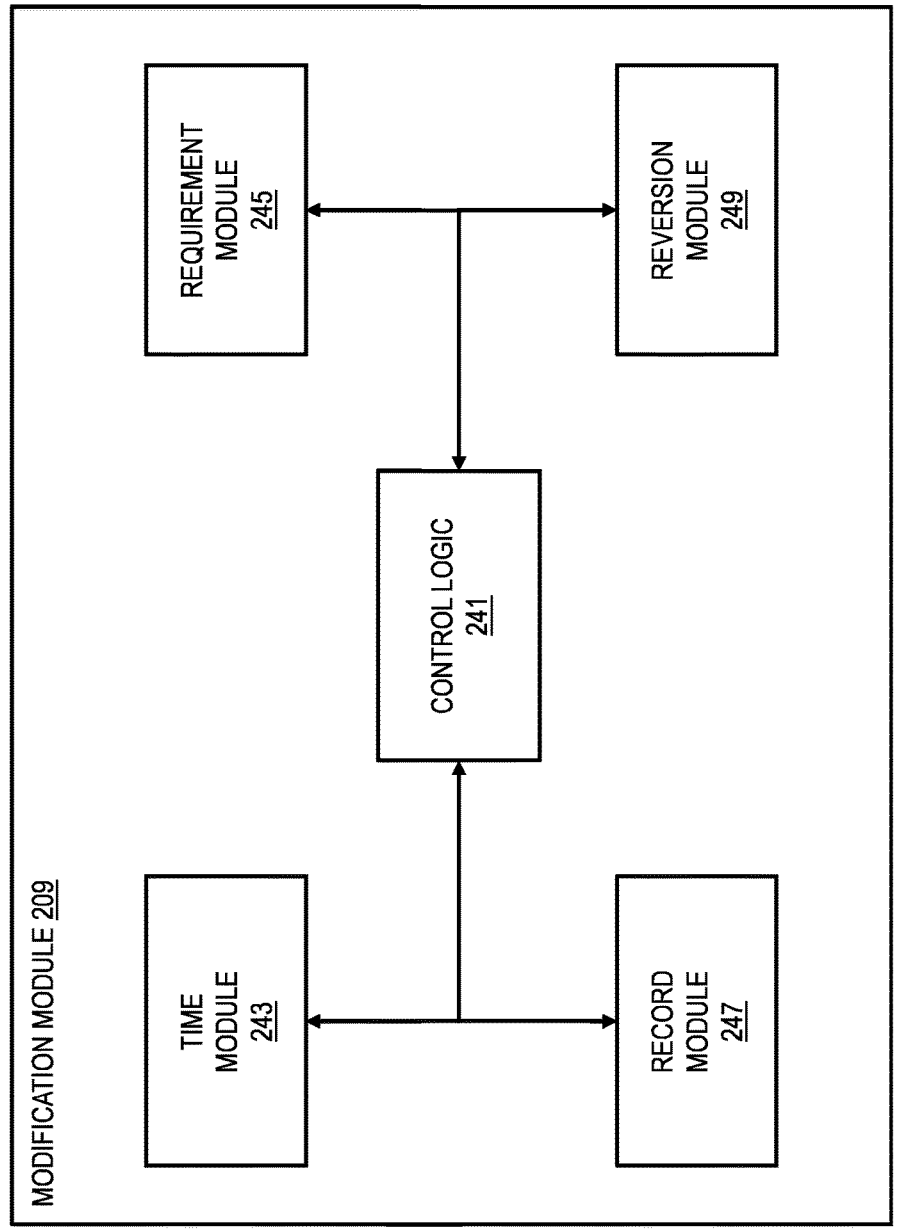
FIG. 2C is a diagram of the components of a modification module, according to one embodiment.

FIG. 2C is a diagram of the components of the modification module 209, according to one embodiment. By way of example, the modification module 209 includes one or more components for determining how to change privacy profiles. It is contemplated that the functions of these components may be combined in one or more components or performed by other components of equivalent functionality. In this embodiment, the modification module 209 includes a control logic 241, a time module 243, a requirement module 245, a record module 247, and a reversion module 249.

In one embodiment, the control logic 241 and the time module 243 may determine the duration of the modification. For example, the system 100 may modify a privacy profile for the duration of the change in physiological states. For instance, a user may change from a physiological state of "calm" to "stressed." The control logic 241 and time module 243 may determine that the user's privacy profile should be modified for the duration that the user is "stressed," before the user's physiological state changes back to "calm." In another embodiment, the system 100 may determine that the modification is for a set period of time. For instance, users and/or the system 100 may set a default expiration time for modifications.

In one scenario, the default expiration time may be set, regardless of the duration of the change in physiological state. One such scenario may include the control logic 241 and time module 243 determining that any modification expires in an hour. In other words, whatever changes were made to a user's privacy settings will revert back to the previous settings, in an hour's time. If system 100 detects that a user is lost and elects to change the user's privacy profile to share his location information, the location information would cease to be shared an hour after the change in physiological state is detected, even if the user is still lost or even if the user found his way after 15 minutes. In another scenario, the default expiration time may be based, at least in part, on the duration of the change in physiological state. One such case may include the control logic 241 and time module 243 setting duration of the modification to be half an hour after the change in physiological state is offset. In the previous example of modifying a user's privacy profile to share a user's location information, this would mean the control logic 241 and time module 243 causing the sharing the user's location information half an hour after the user is observed to have changed back to his "calm" state (after being lost changed his physiological state to "stressed").

In one embodiment, the control logic 241 and requirement module 245 may determine data sharing requirements for candidate user actions. For example, the control logic 241 and requirement module 245 may determine data associated with various candidate actions. The control logic 241 and requirement module 245 may further determine whether how to act on the data, for instance, whether to enable or disable sharing of a certain type of data. For instance, for a physiological state of elevated heart rate where a candidate user action is for a user to cease physical activity, the control logic 241 and requirement module 245 may determine that data sharing requirements may include sending blood pressure information to a doctor. The control logic 241 and requirement module 245 may characterize data sharing requirements as data required to share in order to supplement and/or facilitate candidate actions. Another scenario may include a candidate action being a user taking an exit off a highway to take an alternate route where there is less traffic. Data the user may share to help him achieve this candidate action may include the user's location information. The control logic 241 and requirement module 245 may then identify location information as a data sharing requirement for the candidate action of taking an alternate route.

The distinction between the requirement module 245 and data module 229 may be that the data module 229 (and control logic 221) may determine relationships between actions and particular types of data. Meanwhile, the control logic 241 and requirement module 245 may determine how to act on the data or what modifications are to be made to privacy profiles with respect to the data. For instance, the control logic 221 and data module 229 may determine that the activity, "driving" is associated with "location information." The control logic 241 and requirement module 245 may determine whether to enable or disable sharing of location information.

The control logic 241 and requirement module 245 may further determine who or what to share the information with. For instance, the control logic 241 and requirement module 245 may determine that a family member should receive a user's blood pressure information. Then, the family member may help monitor the user and make sure the user's physical activity is stalled. If the physiological state change persists, the control logic 241 and requirement module 245 may determine that data sharing requirements further extend to sharing the information with a doctor. This way, doctors are notified only where urgent and necessary and users' privacy is guarded to a finer degree. Similarly for the use case with location information, the control logic 241 and requirement module 245 may first determine that data sharing requirements extend to a user's social network or an insurance service that may offer advice on alternate routes. Where this is not effective or advice is unavailable and physiological state change continues, the control logic 241 and requirement module 245 may determine an increase in data sharing requirements, requiring a sharing of location information with a more public map service or wider social network.

In one embodiment, the control logic 241 and record module 247 may make a record of the modification. For example, the control logic 241, time module 243, and record module 247 may track the temporal aspect of a modification. For instance, the control logic 241 and modules may determine if the modification is required only for a specific time period or if it can be retained in the future. The control logic 241 and record module 247 may make a record of a modification where it appears to have coincided with offsetting a negative physiological change. Then, the control logic 241 and record module 247 may access past modifications where similar physiological changes in user activities and/or contexts have occurred before. Also, the control logic 241 and record module 247 may elect to maintain a modification where the modification is expected to be beneficial in the long run. For instance, if a user's blood pressure appears to be high for an extended time, the control logic 241 and record module 247 may determine a modification where the user's blood pressure data is shared with a close family member of the user so that the family member is alerted to any issues.

The control logic 241 and record module 247 may further record a user's response to modifications. For instance, the control logic 241 and record module 247 may present a modification of a privacy profile as a recommendation to a user. For example, the control logic 241 and record module 247 may prompt a display at UEs 101, recommending that a user share some form(s) of data with one or more entities. The recommendations may further include timeframes that limit the duration of the modification. In one embodiment, the control logic 241 and record module 247 may record a user's selections for future reference. For instance, if a user consistently makes the same selections, control logic 241 and record module 247 may automate the modifications or at least auto-populate selections so a user only has to click one button for approval, rather than make each selection each time. In another embodiment, the control logic 241 and record module 247 may make associations between user context and/or activity and her selections so that system 100 may start to predict user preferences regarding modifications.

In one embodiment, the control logic 241 and reversion module 249 may determine a user's privacy profile prior to the modification so that privacy settings. Then, the control logic 241 and reversion module 249 may restore a privacy profile to the data sharing settings (and limits) prior to the modification. In one embodiment, the control logic 241 and reversion module 249 may continually change to a most recent profile, for instance, where users adapt a modification even after negative physiological change has been offset. In another embodiment, the control logic 241 and reversion module 249 may also prompt UEs 101 to display approval for changing back to a privacy profile prior after modifications.

Figure 3:
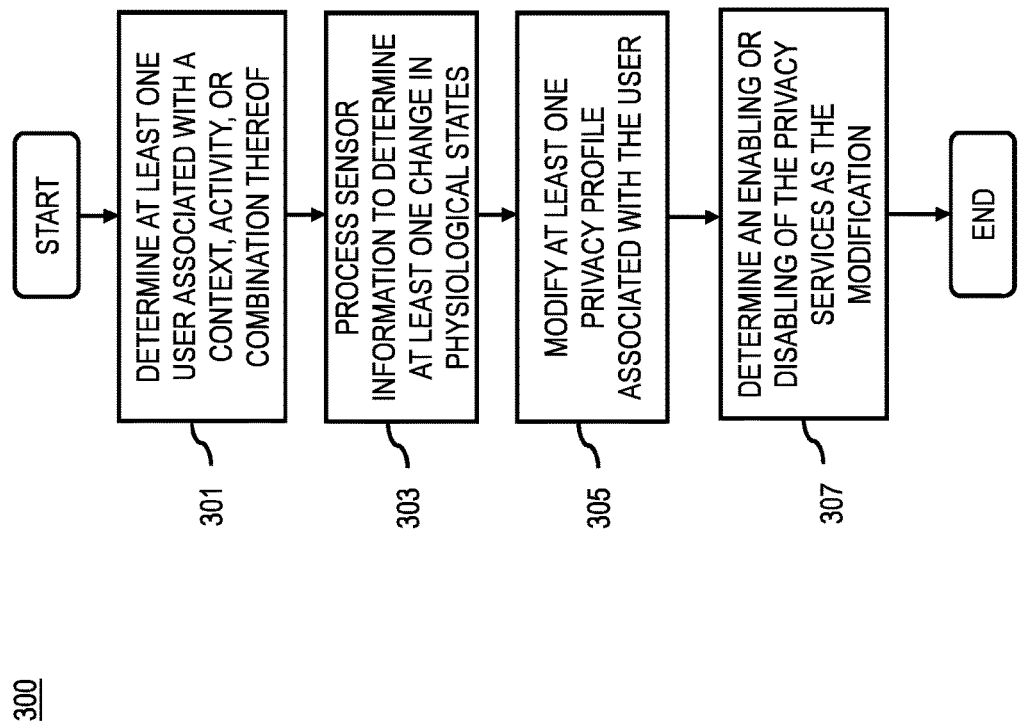
FIG. 3 is a flowchart of a process for adapting a privacy profile based on physiological state changes, according to one embodiment.
Figure 10:
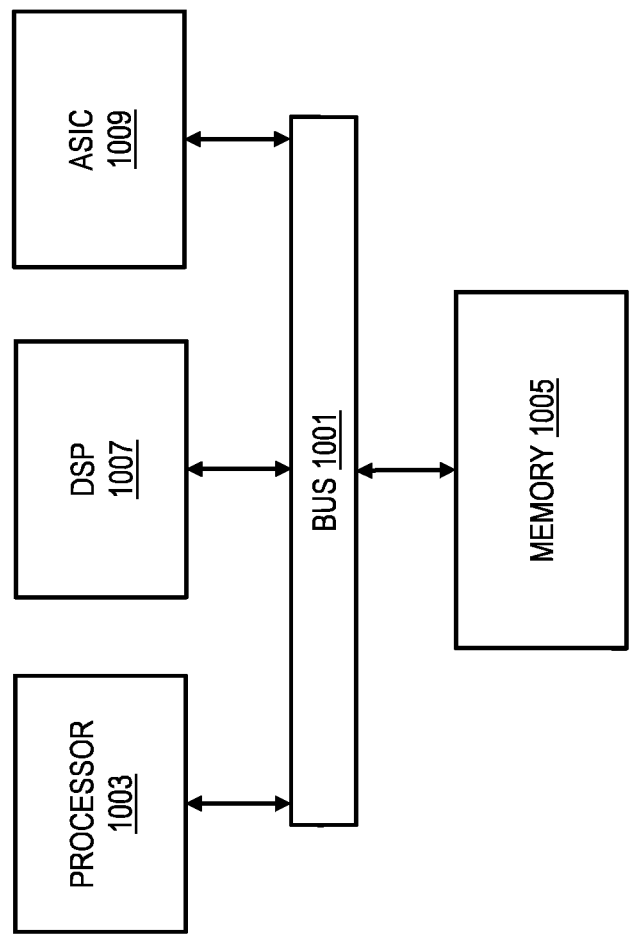
FIG. 10 is a diagram of a chip set that can be used to implement an embodiment of the invention.

FIG. 3 is a flowchart of a process for adapting a privacy profile based on physiological state changes, according to one embodiment. In one embodiment, the control logic 201 performs the process 300 and is implemented in, for instance, a chip set including a processor and a memory as shown in FIG. 10. In step 301, the control logic 201 may determine a user associated with at least one context, at least one activity, or a combination thereof. For example with step 303, the control logic 201 may process and/or facilitate a processing of sensor information to determine at least one change in one or more physiological states of at least one user, wherein the at least one user is associated with at least one context, at least one activity, or a combination thereof. In step 305, the control logic 201 may cause, at least in part, a modification of at least one privacy profile for at least one device associated with the at least one user based, at least in part, on the at least one change in the one or more physiological states, the at least one context, the at least one activity, or a combination thereof.

For example with step 307, the control logic 201 may determine various modifications that act on privacy services. In one embodiment, the modification may be wherein the modification of the at least one privacy profile includes, at least in part, modifying one or more privacy policies operating at least at least one device. In one case, step 307 may include the control logic 201 causing the modification wherein the modification of the at least one privacy profile includes, at least in part, an enabling or a disabling of the one or more privacy service operating at the at least one device. In one embodiment, the modification may include causing, at least in part, a presentation of the modification of the at least one privacy profile as one or more recommendations and determining an input for selecting from among the one or more recommendations to cause, at least in part, an initiation of the modification of the at least one privacy profile.

Figure 4:
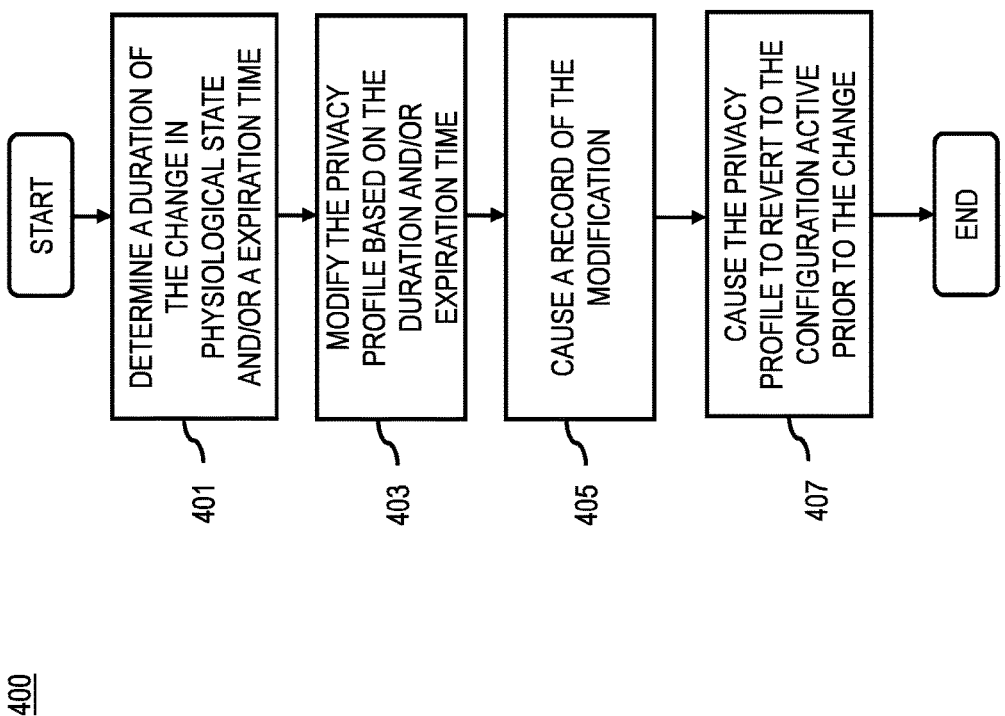
FIG. 4 is a flowchart of a process for determining duration of a modification, according to one embodiment.

FIG. 4 is a flowchart of a process for determining duration of a modification, according to one embodiment. In one embodiment, the control logic 241 performs the process 400 and is implemented in, for instance, a chip set including a processor and a memory as shown in FIG. 10. In steps 401 and 403, the control logic 241 cause, at least in part, an implementation of the modification of the at least one privacy profile for a duration of the at least one change, until an expiration time, or a combination thereof. In step 405, the control logic 241 may cause, at least in part, a record of the modification, wherein a future modification may be based, at least in part, on the record of the modification. For example, for step 407, the control logic 241 may determine the duration of the at least one change, expiration time, or a combination thereof, wherein the at least one privacy profile reverts to at least one configuration active prior to the at least one change in the one or more physiological states.

Figure 5:
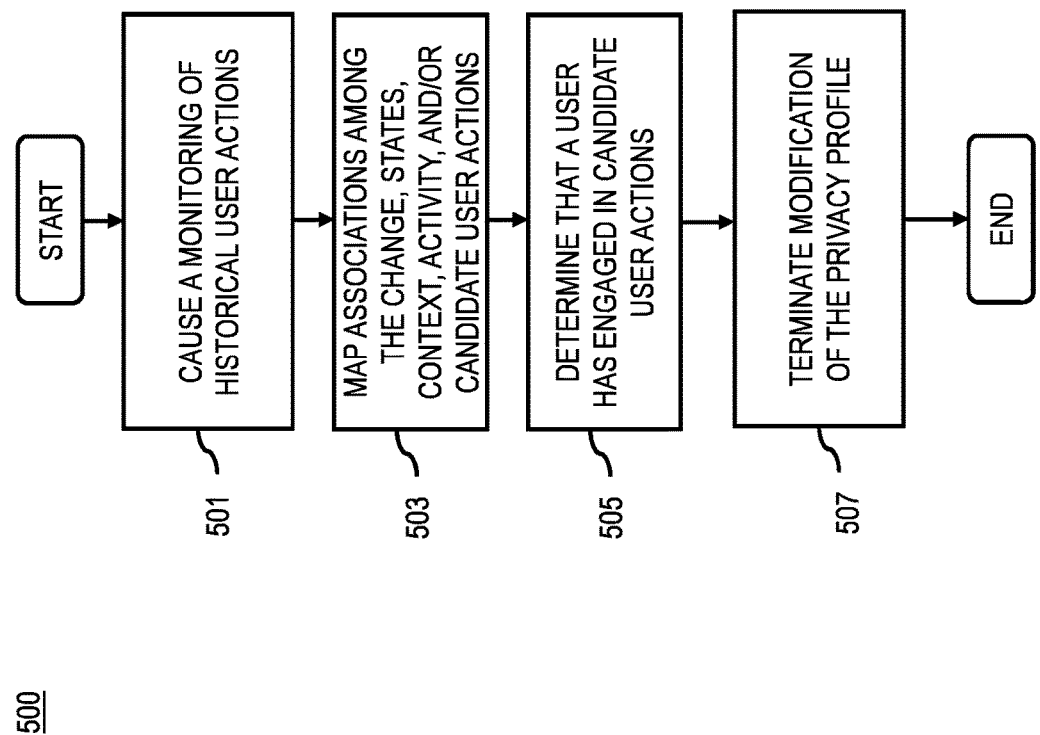
FIG. 5 is a flowchart of a process for determining candidate and historical user actions, according to one embodiment.

FIG. 5 is a flowchart of a process for determining candidate and historical user actions, according to one embodiment. In one embodiment, the control logic 221 performs the process 500 and is implemented in, for instance, a chip set including a processor and a memory as shown in FIG. 10. For step 501, the control logic 221 may cause, at least in part, a monitoring of one or more historical user actions associated with the one or more physiological states, the at least one context, the at least one activity, or a combination thereof. Then for step 503, the control logic 221 may receive an input for specifying a mapping of one or more associations among the at least one change, the one or more physiological states, that at least one context, the at least one activity, one or more candidate user actions, or a combination thereof. For example, the mapping of associations may include a matrix reflecting various associations among physiological states, contexts, activities, and/or candidate user actions.

In one embodiment, step 505 may include determining the one or more candidate user actions following the change in the one or more physiological states, wherein the one or more candidate user actions are mapped as one or more offsetting actions for the at least one change in the one or more physiological states. In one embodiment, step 507 may include causing, at least in part, a termination of the modification of the at least one privacy profile. For example, the termination may be based on a determination that one of the candidate actions has occurred.

Figure 6:
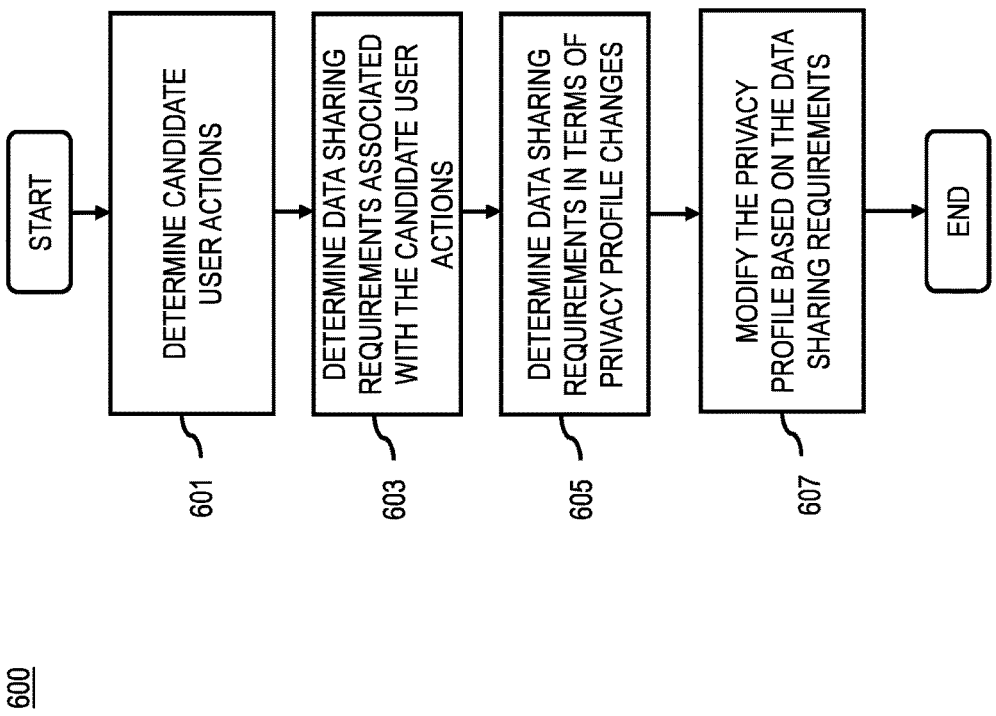
FIG. 6 is a flowchart of a process for determining one or more data sharing requirements regarding the modifications, according to one embodiment.

FIG. 6 is a flowchart of a process for determining one or more data sharing requirements regarding the modifications, according to one embodiment. In one embodiment, the control logic 241 performs the process 600 and is implemented in, for instance, a chip set including a processor and a memory as shown in FIG. 10. In one embodiment, the control logic 241 may determine candidate user actions with step 601. Then with step 603, the control logic 241 may determine one or more data sharing requirements for the one or more candidate user actions. For step 605, the control logic 241 may determine changes to data sharing requirements with respect to privacy profiles and then for step 607, the control logic 241 may determine the changes wherein the modification of the at least one privacy profile is further based, at least in part, on the one or more data sharing requirements.

Figure 7:
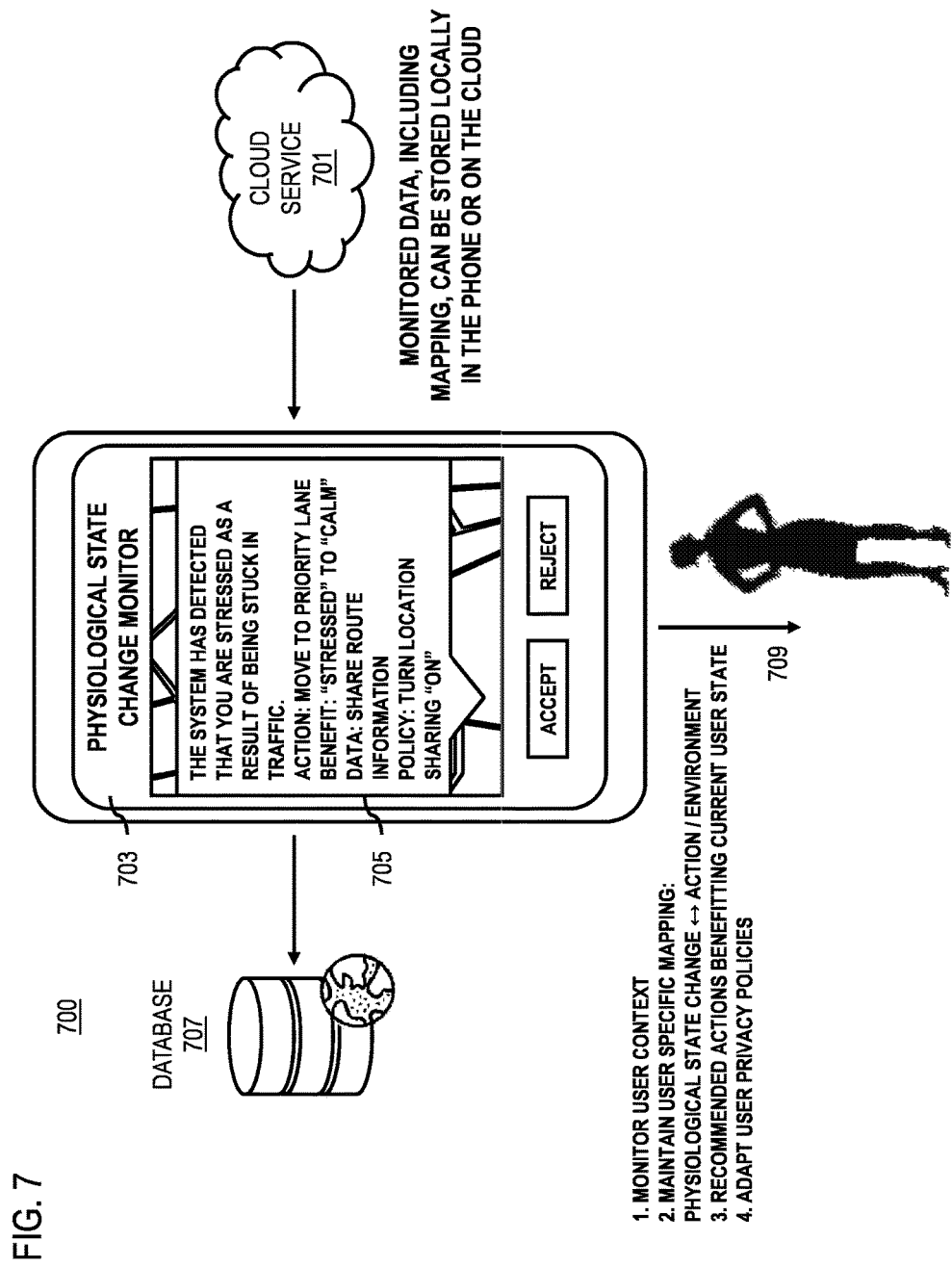
FIG. 7 is a diagram of a use case, according to one embodiment.

FIG. 7 is a diagram of a use case 700, in one embodiment. For example, the system 100 may continually monitor user data via a cloud service 701. The cloud service 701 may monitor data on a user's physiological state, activity, and/or context. In one embodiment, the cloud service 701 may further map these three fields to each other, creating associations among the changes in physiological states, physiological states, context, activities, and candidate user actions. System 100 may connect users to knowledge from cloud service 701 via an application, for instance, physiological state change monitor 703. In one embodiment, the monitor 703 may present modifications to policy profiles in the form of a recommendation 705. For example, the recommendation 705 may present a user's change in physiological state, one or more candidate actions, one or more types of data whose sharing may be enabled or disabled, and a policy profile modification. In one embodiment, recommendation 705 may include "accept" and "reject" buttons for users to approve the modifications.

In a further embodiment, database 707 may include generic behavioral data from which the monitor 703 may derive candidate actions. With a user's reaction 709 to the recommendation 705, the system 100 may continually maintain and update user-specific mapping of physiological state change to the action and context. The system 100 may further adapt user privacy profiles or offer candidate actions that reflect a specific user's preferences.

Figure 8:
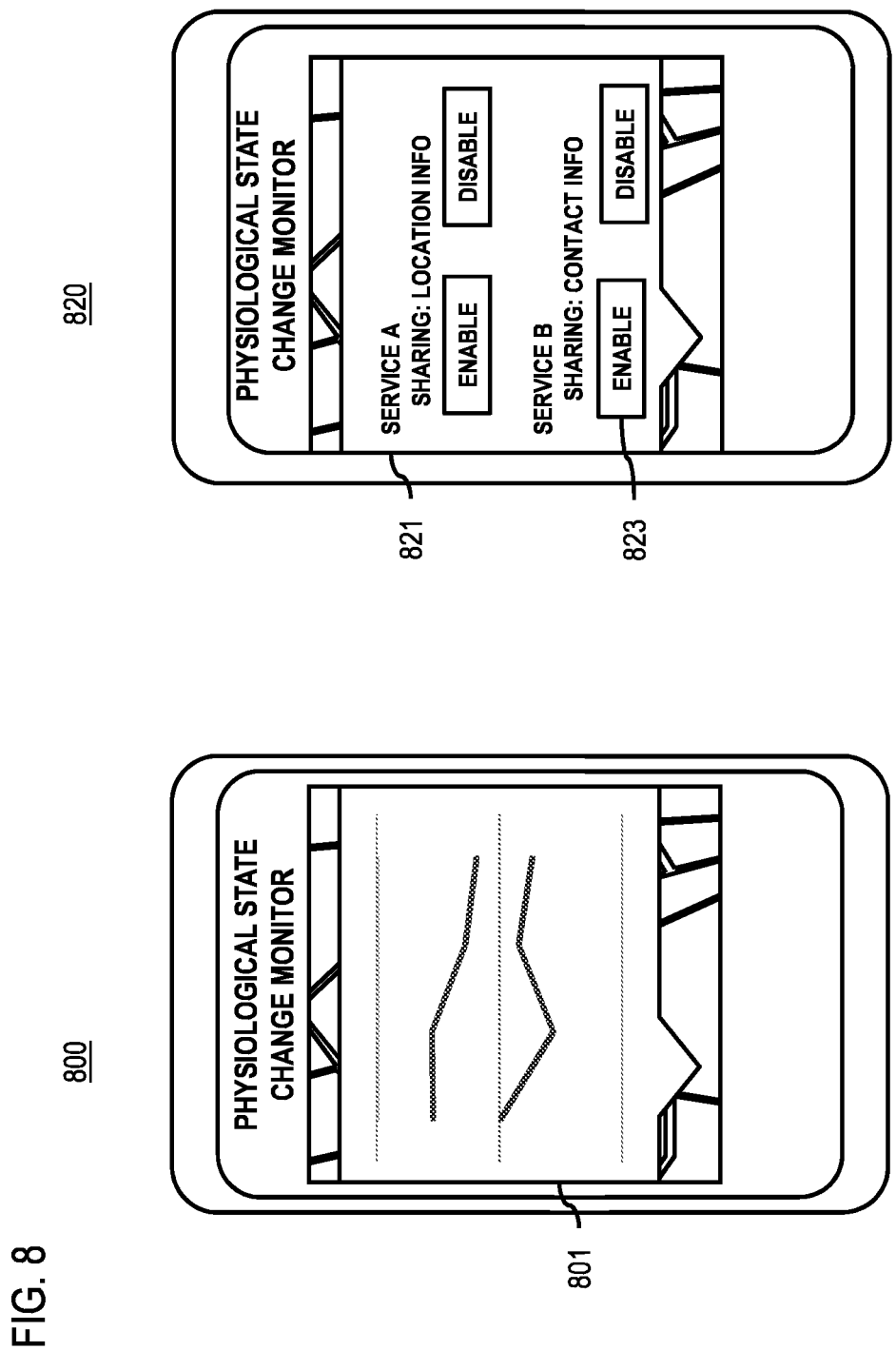
FIG. 8 is a diagram of user interfaces for modifications to privacy profiles, according to one embodiment.

FIG. 8 presents user interfaces 800 and 820 for the modifications to privacy profiles, in one embodiment. For user interface 800, system 100 may present a chart of changes to physiological states. For example, chart 801 may show a trend of decreased anxiety over the course of a month based on changes to privacy profiles. In one case, a user may then elect to adapt the modification as his new privacy profile with respect to a service since the modification had such a positive impact on his physiological state. User interface 820 may include an overview 821 of privacy profiles for various services. For example, user interface 820 may include a display listing various services and data that is shared with each service. Users may then elect to enable and/or disable the sharing, for example, with enable button 823. In one embodiment, users may be presented with user interface 820 as part of initiation of a service, for example, where a user enters his initial privacy settings. In the alternative, user interface 820 may appear where a user wants to see a summary of modifications and possibly reset sharing requirements. In a further embodiment, user interface 820 may include duration and/or display preferences for various services' modifications.

The processes described herein for adapting privacy profiles to respond to changes in physiological states may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 9:
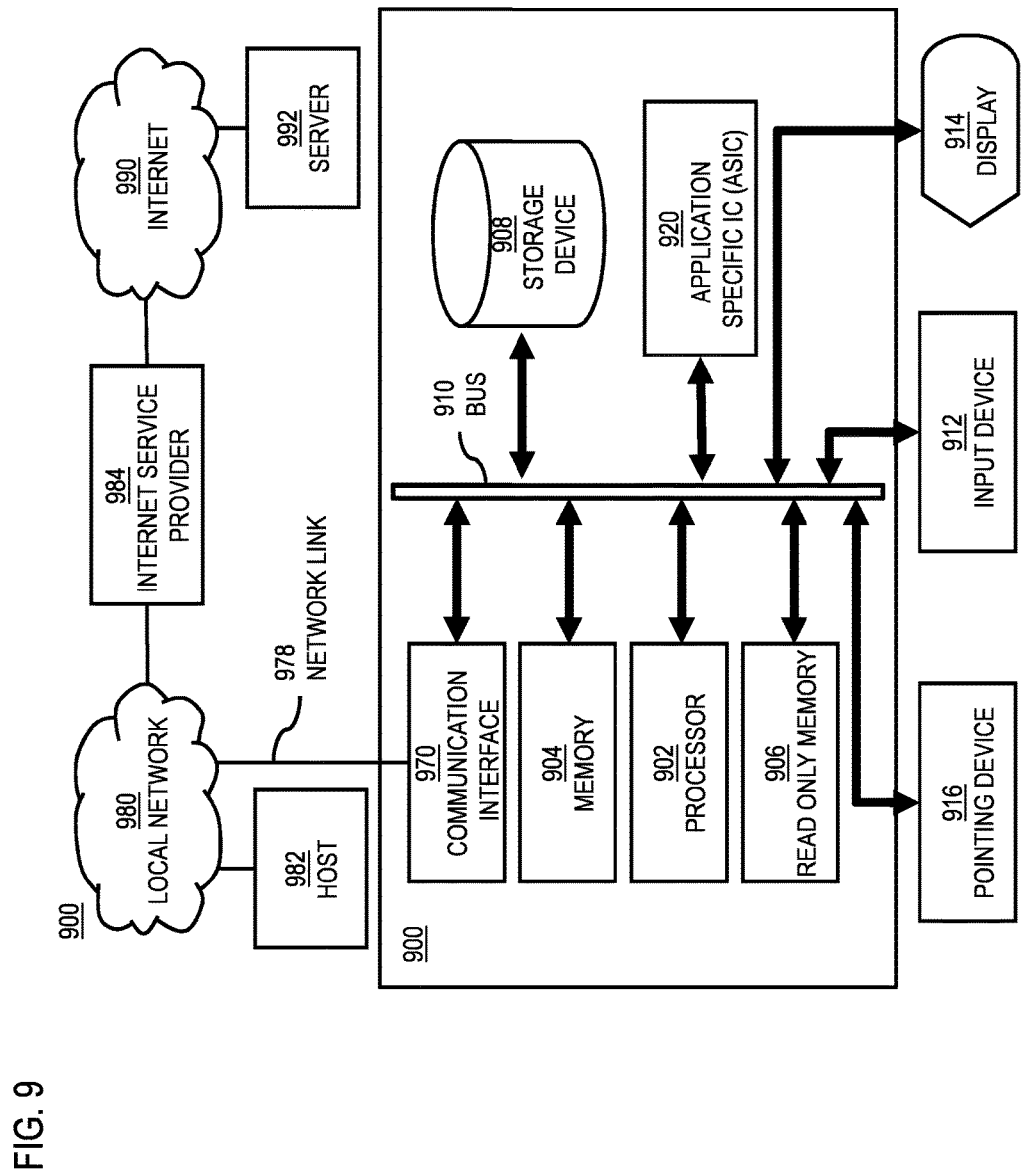
FIG. 9 is a diagram of hardware that can be used to implement an embodiment of the invention.

FIG. 9 illustrates a computer system 900 upon which an embodiment of the invention may be implemented. Although computer system 900 is depicted with respect to a particular device or equipment, it is contemplated that other devices or equipment (e.g., network elements, servers, etc.) within FIG. 9 can deploy the illustrated hardware and components of system 900. Computer system 900 is programmed (e.g., via computer program code or instructions) to adapt privacy profiles to respond to changes in physiological states as described herein and includes a communication mechanism such as a bus 910 for passing information between other internal and external components of the computer system 900. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of adapting privacy profiles to respond to changes in physiological states.

A bus 910 includes one or more parallel conductors of information so that information is transferred quickly among devices coupled to the bus 910. One or more processors 902 for processing information are coupled with the bus 910.

A processor (or multiple processors) 902 performs a set of operations on information as specified by computer program code related to adapting privacy profiles to respond to changes in physiological states. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 910 and placing information on the bus 910. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 902, such as a sequence of operation codes, constitute processor instructions, also called computer system instructions or, simply, computer instructions. Processors may be implemented as mechanical, electrical, magnetic, optical, chemical, or quantum components, among others, alone or in combination.

Computer system 900 also includes a memory 904 coupled to bus 910. The memory 904, such as a random access memory (RAM) or any other dynamic storage device, stores information including processor instructions for adapting privacy profiles to respond to changes in physiological states. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of processor instructions. The computer system 900 also includes a read only memory (ROM) 906 or any other static storage device coupled to the bus 910 for storing static information, including instructions, that is not changed by the computer system 900. Some memory is composed of volatile storage that loses the information stored thereon when power is lost. Also coupled to bus 910 is a non-volatile (persistent) storage device 908, such as a magnetic disk, optical disk or flash card, for storing information, including instructions, that persists even when the computer system 900 is turned off or otherwise loses power.

Information, including instructions for adapting privacy profiles to respond to changes in physiological states, is provided to the bus 910 for use by the processor from an external input device 912, such as a keyboard containing alphanumeric keys operated by a human user, a microphone, an Infrared (IR) remote control, a joystick, a game pad, a stylus pen, a touch screen, or a sensor. A sensor detects conditions in its vicinity and transforms those detections into physical expression compatible with the measurable phenomenon used to represent information in computer system 900. Other external devices coupled to bus 910, used primarily for interacting with humans, include a display device 914, such as a cathode ray tube (CRT), a liquid crystal display (LCD), a light emitting diode (LED) display, an organic LED (OLED) display, a plasma screen, or a printer for presenting text or images, and a pointing device 916, such as a mouse, a trackball, cursor direction keys, or a motion sensor, for controlling a position of a small cursor image presented on the display 914 and issuing commands associated with graphical elements presented on the display 914, and one or more camera sensors 994 for capturing, recording and causing to store one or more still and/or moving images (e.g., videos, movies, etc.) which also may comprise audio recordings. In some embodiments, for example, in embodiments in which the computer system 900 performs all functions automatically without human input, one or more of external input device 912, display device 914 and pointing device 916 may be omitted.

In the illustrated embodiment, special purpose hardware, such as an application specific integrated circuit (ASIC) 920, is coupled to bus 910. The special purpose hardware is configured to perform operations not performed by processor 902 quickly enough for special purposes. Examples of ASICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a one-way or two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. For wireless links, the communications interface 970 sends or receives or both sends and receives electrical, acoustic or electromagnetic signals, including infrared and optical signals, that carry information streams, such as digital data. For example, in wireless handheld devices, such as mobile telephones like cell phones, the communications interface 970 includes a radio band electromagnetic transmitter and receiver called a radio transceiver. In certain embodiments, the communications interface 970 enables connection to the communication network 105 for adapting privacy profiles to respond to changes in physiological states to the UE 101.

The term "computer-readable medium" as used herein refers to any medium that participates in providing information to processor 902, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 908. Volatile media include, for example, dynamic memory 904. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 920.

Network link 978 typically provides information communication using transmission media through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990.

A computer called a server host 992 connected to the Internet hosts a process that provides a service in response to information received over the Internet. For example, server host 992 hosts a process that provides information representing video data for presentation at display 914. It is contemplated that the components of system 900 can be deployed in various configurations within other computer systems, e.g., host 982 and server 992.

At least some embodiments of the invention are related to the use of computer system 900 for implementing some or all of the techniques described herein. According to one embodiment of the invention, those techniques are performed by computer system 900 in response to processor 902 executing one or more sequences of one or more processor instructions contained in memory 904. Such instructions, also called computer instructions, software and program code, may be read into memory 904 from another computer-readable medium such as storage device 908 or network link 978. Execution of the sequences of instructions contained in memory 904 causes processor 902 to perform one or more of the method steps described herein. In alternative embodiments, hardware, such as ASIC 920, may be used in place of or in combination with software to implement the invention. Thus, embodiments of the invention are not limited to any specific combination of hardware and software, unless otherwise explicitly stated herein.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server host 992 transmits program code for a particular application, requested by a message sent from computer 900, through Internet 990, ISP equipment 984, local network 980 and communications interface 970. The received code may be executed by processor 902 as it is received, or may be stored in memory 904 or in storage device 908 or any other non-volatile storage for later execution, or both. In this manner, computer system 900 may obtain application program code in the form of signals on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

FIG. 10 illustrates a chip set or chip 1000 upon which an embodiment of the invention may be implemented. Chip set 1000 is programmed to adapt privacy profiles to respond to changes in physiological states, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 1000 can be implemented in a single chip. It is further contemplated that in certain embodiments the chip set or chip 1000 can be implemented as a single "system on a chip." It is further contemplated that in certain embodiments a separate ASIC would not be used, for example, and that all relevant functions as disclosed herein would be performed by a processor or processors. Chip set or chip 1000, or a portion thereof, constitutes a means for performing one or more steps of providing user interface navigation information associated with the availability of functions. Chip set or chip 1000, or a portion thereof, constitutes a means for performing one or more steps of adapting privacy profiles to respond to changes in physiological states.

In one embodiment, the chip set or chip 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a more general purpose processor. Other specialized components to aid in performing the inventive functions described herein may include one or more field programmable gate arrays (FPGA), one or more controllers, or one or more other special-purpose computer chips.

In one embodiment, the chip set or chip 1000 includes merely one or more processors and some software and/or firmware supporting and/or relating to and/or for the one or more processors.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform the inventive steps described herein to adapt privacy profiles to respond to changes in physiological states. The memory 1005 also stores the data associated with or generated by the execution of the inventive steps.

FIG. 11 is a diagram of exemplary components of a mobile terminal (e.g., handset) for communications, which is capable of operating in the system of FIG. 1, according to one embodiment. In some embodiments, mobile terminal 1101, or a portion thereof, constitutes a means for performing one or more steps of adapting privacy profiles to respond to changes in physiological states. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1103, a Digital Signal Processor (DSP) 1105, and a receiver/transmitter unit including a microphone gain control unit and a speaker gain control unit. A main display unit 1107 provides a display to the user in support of various applications and mobile terminal functions that perform or support the steps of adapting privacy profiles to respond to changes in physiological states. The display 1107 includes display circuitry configured to display at least a portion of a user interface of the mobile terminal (e.g., mobile telephone). Additionally, the display 1107 and display circuitry are configured to facilitate user control of at least some functions of the mobile terminal. An audio function circuitry 1109 includes a microphone 1111 and microphone amplifier that amplifies the speech signal output from the microphone 1111. The amplified speech signal output from the microphone 1111 is fed to a coder/decoder (CODEC) 1113.

A radio section 1115 amplifies power and converts frequency in order to communicate with a base station, which is included in a mobile communication system, via antenna 1117. The power amplifier (PA) 1119 and the transmitter/modulation circuitry are operationally responsive to the MCU 1103, with an output from the PA 1119 coupled to the duplexer 1121 or circulator or antenna switch, as known in the art. The PA 1119 also couples to a battery interface and power control unit 1120.

In use, a user of mobile terminal 1101 speaks into the microphone 1111 and his or her voice along with any detected background noise is converted into an analog voltage. The analog voltage is then converted into a digital signal through the Analog to Digital Converter (ADC) 1123. The control unit 1103 routes the digital signal into the DSP 1105 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 1125 for compensation of any frequency-dependent impairments that occur during transmission though the air such as phase and amplitude distortion. After equalizing the bit stream, the modulator 1127 combines the signal with a RF signal generated in the RF interface 1129. The modulator 1127 generates a sine wave by way of frequency or phase modulation. In order to prepare the signal for transmission, an up-converter 1131 combines the sine wave output from the modulator 1127 with another sine wave generated by a synthesizer 1133 to achieve the desired frequency of transmission. The signal is then sent through a PA 1119 to increase the signal to an appropriate power level. In practical systems, the PA 1119 acts as a variable gain amplifier whose gain is controlled by the DSP 1105 from information received from a network base station. The signal is then filtered within the duplexer 1121 and optionally sent to an antenna coupler 1135 to match impedances to provide maximum power transfer. Finally, the signal is transmitted via antenna 1117 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 1101 are received via antenna 1117 and immediately amplified by a low noise amplifier (LNA) 1137. A down-converter 1139 lowers the carrier frequency while the demodulator 1141 strips away the RF leaving only a digital bit stream. The signal then goes through the equalizer 1125 and is processed by the DSP 1105. A Digital to Analog Converter (DAC) 1143 converts the signal and the resulting output is transmitted to the user through the speaker 1145, all under control of a Main Control Unit (MCU) 1103 which can be implemented as a Central Processing Unit (CPU).

The MCU 1103 receives various signals including input signals from the keyboard 1147. The keyboard 1147 and/or the MCU 1103 in combination with other user input components (e.g., the microphone 1111) comprise a user interface circuitry for managing user input. The MCU 1103 runs a user interface software to facilitate user control of at least some functions of the mobile terminal 1101 to adapt privacy profiles to respond to changes in physiological states. The MCU 1103 also delivers a display command and a switch command to the display 1107 and to the speech output switching controller, respectively. Further, the MCU 1103 exchanges information with the DSP 1105 and can access an optionally incorporated SIM card 1149 and a memory 1151. In addition, the MCU 1103 executes various control functions required of the terminal. The DSP 1105 may, depending upon the implementation, perform any of a variety of conventional digital processing functions on the voice signals. Additionally, DSP 1105 determines the background noise level of the local environment from the signals detected by microphone 1111 and sets the gain of microphone 1111 to a level selected to compensate for the natural tendency of the user of the mobile terminal 1101.

The CODEC 1113 includes the ADC 1123 and DAC 1143. The memory 1151 stores various data including call incoming tone data and is capable of storing other data including music data received via, e.g., the global Internet. The software module could reside in RAM memory, flash memory, registers, or any other form of writable storage medium known in the art. The memory device 1151 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1149 carries, for instance, important information, such as the cellular phone number, the carrier supplying service, subscription details, and security information. The SIM card 1149 serves primarily to identify the mobile terminal 1101 on a radio network. The card 1149 also contains a memory for storing a personal telephone number registry, text messages, and user specific mobile terminal settings.

Further, one or more camera sensors 1153 may be incorporated onto the mobile station 1101 wherein the one or more camera sensors may be placed at one or more locations on the mobile station. Generally, the camera sensors may be utilized to capture, record, and cause to store one or more still and/or moving images (e.g., videos, movies, etc.) which also may comprise audio recordings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising:
    receiving, at a user device, a matrix mapping at least one change in one or more physiological states of a user of the user device with one or more user actions having one or more offsetting effects on the at least one change, wherein the at least one change in the one or more physiological states is caused, at least in part, by stress;
    determining, at the user device, at least one private data sharing requirement of the user to facilitate the one or more user actions, wherein the at least one private data sharing requirement specifies private data sharing settings in a privacy profile of the user;
    upon determining based on sensor information of the user device that the at least one change in the one or more physiological states occurs, retrieving, at the user device, the one or more user actions and the at least one private data sharing requirement;
    modifying the privacy profile of the user at the user device to facilitate the at least one private data sharing requirement;
    implementing the modification of the privacy profile for a duration of the at least one change, until an expiration time, or a combination thereof, wherein the matrix and the privacy profile are specific to the user; and
    monitoring, via the user device, whether the one or more user actions occur, and whether the at least one change in the one or more physiological states is offset after the modification,
    wherein the privacy profile reverts to at least one configuration active prior to the at least one change in the one or more physiological states, after the at least one change is offset after the modification; and
    wherein the one or more user actions are external to and independent from the user device.

2. A method of claim 1, further comprising:
    initiating a storage of a record of the modification,
    wherein a future modification may be based, at least in part, on the record of the modification.

3. A method of claim 1, further comprising:
    receiving an input for specifying one or more other associations among the at least one change, the one or more physiological states, the one or more user actions, or a combination thereof.

4. A method of claim 1, further comprising:
    monitoring one or more historical user actions associated with at least one change in one or more physiological states,
    wherein the matrix is determined based on the one or more historical user actions using clustering, mining, one or more behavioral models, or a combination thereof.

5. A method of claim 1, further comprising:
    determining that the one or more user actions have occurred, that the at least one change in the one or more physiological states is offset after the modification, or a combination thereof; and
    initiating a termination of the modification of the privacy profile based on the determination.

6. A method of claim 1, further comprising:
    initiating a presentation of the modification of the privacy profile as one or more recommendations; and
    determining an input for selecting from among the one or more recommendations to cause, at least in part, an initiation of the modification of the privacy profile.

7. A method of claim 1, wherein the at least one private data sharing requirement involves sharing an identification, an age, a location, or a combination thereof, of the user.

8. An apparatus comprising:
    at least one processor; and
    at least one memory including computer program code for one or more programs, the at least one memory and the computer program code configured to, with the at least one processor, cause the apparatus embedded in a user device to perform at least the following, receive a matrix mapping at least one change in one or more physiological states of a user of the user device with one or more user actions coincided with one or more offsetting effects on the at least one change;

determine at least one private data sharing requirement of the user to facilitate the one or more user actions, wherein the at least one private data sharing requirement specifies private data sharing settings in a privacy profile of the user;

upon determining based on sensor information of the user device that the at least one change in the one or more physiological states occurs, retrieve the one or more user actions and the at least one private data sharing requirement;

modify the privacy profile of the user at the user device to facilitate the at least one private data sharing requirement;

implement the modification of the privacy profile for a duration of the at least one change, until an expiration time, or a combination thereof; and monitor whether the one or more user actions occur, and whether the at least one change in the one or more physiological states is offset after the modification, wherein the privacy profile reverts to at least one configuration active prior to the at least one change in the one or more physiological states, after the at least one change is offset after the modification; and wherein the one or more user actions are external to and independent from the user device.

9. An apparatus of claim 8, wherein the apparatus is further caused to:
    initiate a storage of a record of the modification,
    wherein a future modification may be based, at least in part, on the record of the modification.

10. An apparatus of claim 8, wherein the apparatus is further caused to:
    receive an input for specifying one or more other associations among the at least one change, the one or more physiological states, the one or more user actions, or a combination thereof.

11. An apparatus of claim 10, wherein the matrix is determined using clustering, mining, one or more behavioral models, or a combination thereof.

12. An apparatus of claim 10, wherein the apparatus is further caused to:
    initiate a termination of the modification of the privacy profile, after the at least one change in the one or more physiological states is offset.

13. An apparatus of claim 8, wherein the apparatus is further caused to:
    initiating a presentation of the modification of the privacy profile as one or more recommendations; and
    determine an input for selecting from among the one or more recommendations to cause, at least in part, an initiation of the modification of the privacy profile.

14. An apparatus of claim 8, wherein the at least one private data sharing requirement involves sharing an identification, an age, a location, or a combination thereof, of the user.

* * * * *

UNITED STATES PATENT AND TRADEMARK OFFICE
CERTIFICATE OF CORRECTION

PATENT NO. : 9,946,893 B2
APPLICATION NO. : 14/090674
DATED : April 17, 2018
INVENTOR(S) : Julian Nolan et al.

It is certified that error appears in the above-identified patent and that said Letters Patent is hereby corrected as shown below:

In the Claims

Column 25, Line 61, cancel the text beginning with "1. A method comprising:" to and ending "user device." in Column 26, Line 27, and insert the following claim:
--1. A method comprising: receiving, at a user device, a matrix mapping at least one change in one or more physiological states of a user of the user device with one or more user actions coincided with one or more offsetting effects on the at least one change, wherein the at least one change in the one or more physiological states is caused, at least in part, by stress; determining, at the user device, at least one private data sharing requirement of the user to facilitate the one or more user actions, wherein the at least one private data sharing requirement specifies private data sharing settings in a privacy profile of the user; upon determining based on sensor information of the user device that the at least one change in the one or more physiological states occurs, retrieving, at the user device, the one or more user actions and the at least one private data sharing requirement; modifying the privacy profile of the user at the user device to facilitate the at least one private data sharing requirement; implementing the modification of the privacy profile for a duration of the at least one change, until an expiration time, or a combination thereof, wherein the matrix and the privacy profile are specific to the user; and monitoring, via the user device, whether the one or more user actions occur, and whether the at least one change in the one or more physiological states is offset after the modification, wherein the privacy profile reverts to at least one configuration active prior to the at least one change in the one or more physiological states, after the at least one change is offset after the modification; and wherein the one or more user actions are external to and independent from the user device.--

Column 26, Line 64, cancel the text beginning with "8. An apparatus comprising:" to and ending "user device." in Column 28, Line 2, and insert the following claim:
--8. An apparatus comprising: at least one processor; and at least one memory including computer program code for one or more programs, the at least one memory and the computer program code configured to, with the at least one processor, cause the apparatus embedded in a user device to perform at least the following, receive a matrix mapping at least one change in one or more physiological states of a user of the user device with one or more user actions coincided with one or more offsetting effects on the at least one change; determine at least one private data sharing Signed and Sealed this
Third Day of July, 2018

Andrei Iancu
*Director of the United States Patent and Trademark Office*

CERTIFICATE OF CORRECTION (continued)
U.S. Pat. No. 9,946,893 B2 requirement of the user to facilitate the one or more user actions, wherein the at least one private data sharing requirement specifies private data sharing settings in a privacy profile of the user; upon determining based on sensor information of the user device that the at least one change in the one or more physiological states occurs, retrieve the one or more user actions and the at least one private data sharing requirement; modify the privacy profile of the user at the user device to facilitate the at least one private data sharing requirement; implement the modification of the privacy profile for a duration of the at least one change, until an expiration time, or a combination thereof; and monitor whether the one or more user actions occur, and whether the at least one change in the one or more physiological states is offset after the modification, wherein the privacy profile reverts to at least one configuration active prior to the at least one change in the one or more physiological states, after the at least one change is offset after the modification; and wherein the one or more user actions are external to and independent from the user device.--